(12) United States Patent
Rudnick et al.

(10) Patent No.: US 6,313,075 B1
(45) Date of Patent: Nov. 6, 2001

(54) ALKYLATED THIANTHRENE LUBRICANTS

(76) Inventors: Leslie R. Rudnick, 5 Winthrop Rd., Lawrenceville, NJ (US) 08648; Carleton N. Rowe, 303 Lenape Trail, Wenonah, NJ (US) 08090

(*) Notice: Subject to any disclaimer, the term of this patent is extended or adjusted under 35 U.S.C. 154(b) by 0 days.

(21) Appl. No.: 07/752,138

(22) Filed: Aug. 29, 1991

(51) Int. Cl.$^7$ ............... C10M 105/72; C10M 135/34; C07D 339/08
(52) U.S. Cl. ............................. 508/301; 549/17
(58) Field of Search ............... 252/45; 549/17; 508/301

(56) References Cited

U.S. PATENT DOCUMENTS

| | | | |
|---|---|---|---|
| 2,213,804 | * 4/1940 | Lincoln | 252/45 |
| 4,891,448 | * 1/1990 | Garces | 585/452 |
| 5,034,563 | * 7/1991 | Ashjian et al. | 585/467 |
| 5,171,915 | * 12/1992 | Forbus et al. | 585/464 |

OTHER PUBLICATIONS

Morrison and Boyd, "Organic Chemistry", Fourth Edition, p. 632, (date unknown).*

* cited by examiner

Primary Examiner—Jerry D. Johnson

(57) ABSTRACT

Alkylated thianthrenes are high temperature stable lubricant fluids having excellent thermal stability, antiwear and load-carrying properties and excellent additive solubility as well as multifunctional additives for fuels.

8 Claims, No Drawings

ALKYLATED THIANTHRENE LUBRICANTS

CROSS-REFERENCE TO RELATED APPLICATIONS

This application is related to Ser. No. 07/637,425 filed on Jan. 4, 1991; Ser. No. 07/639,861 filed on Jan. 11, 1991; Ser. No. 07/686,454 filed on Apr. 17, 1991; Ser. No. 07/686,453 filed on Apr. 17, 1991; Ser. No. 07/686,452 filed on Apr. 17, 1991; Ser. No. 07/701,900 filed on May 17, 1991; and Ser. No. 07/705,997 filed on May 28, 1991.

BACKGROUND OF THE INVENTION

1. Field of the Invention

This invention is directed to improved lubricant compositions comprising alkylated thianthrene lubricant fluids alone or in combination with synthetic or mineral oils, and to mineral or synthetic lubricant oil or hydrocarbyl or hydrocarbloxy fuel compositions containing minor amounts of said alkylated thianthrenes as multifunctional additives therefor.

2. Description of Related Art

Polyphenyl sulfides are known and have been used as lubricants/additives in special applications, Polyphenyl sulfides suffer from very high cost due to difficult synthesis and have poor low-temperature properties.

Incorporation of linear alkyl groups into diphenyl sulfide eliminates both of the above problems and provides a novel, relatively inexpensive lubricant having excellent low-temperature properties. The use of these adducts as a lubricant or lubricant additive in either mineral or synthetic lubricants has been recently disclosed as noted in one of the above copending applications.

The principal limitation of getting monoalkylated fluids of diphenyl sulfide using octadecene or lower olefins having greater than 5 cSt viscosity at 100° C. limits end use applications. However, alkylation of thianthrene with hexadecene provides a monoalkylated adduct having a viscosity of >12 cSt. This opens a wider range of application areas for this novel lubricating fluid.

The preparation and use of alkylated thianthrenes as a new class of lubricating fluids is disclosed in the instant application. These fluids have the advantages of alkylated diphenyl sulfides in that the polar sulfur provides excellent additive solubility and good lubricating properties.

BRIEF SUMMARY OF THE INVENTION

This application is directed to novel lubricant compositions comprising from about less than one percent to about 100% of alkylated thianthrenes as disclosed herein and to mineral and synthetic lubricants and fuels containing minor proportions of the disclosed thianthrenes as multifunctional additives.

The products obtained from the reaction of a linear olefin and thianthrene in the presence of specific zeolite catalysts are unique not only in composition and structure but in utility. Part of the uniqueness may be derived from the specific reaction over zeolite catalysts; generally, they have a higher VI at a given viscosity. The incorporation of various alkyl groups into the thianthrene structure provides compositions of different viscosity and low temperature viscometrics.

The thermal stability of these alkylated thianthrenes is excellent and believed to be improved over materials of branched structure due to the facility for carbon-carbon bond breaking in the latter materials.

These unique lubricants exhibit beneficial properties from the unique reaction of olefin with the thianthrene structure in such a way as to remain predominantly linear. This is a direct result of the catalytic reaction. This combination provides for the novel structural class disclosed here. The use of these compositions of matter as either functionalized alkyl thianthrene lubricant fluids or lubricant additives is believed to be novel.

The use of these adducts as a lubricant or lubricant additive in either mineral or synthetic lubricants is unique and provides improved properties and performance benefits due to inherent synergism. It is expected that the performance benefits will include antifatigue, antispalling, antistaining, antisquawking, improved additive solubility, improved load carrying/bearing, extreme pressure, improved thermal and oxidative stability, friction reducing, antiwear, anticorrosion, cleanliness improving, low- and high-temperature antioxidant, demulsifying, emulsifying and detergency properties.

It is therefore an object of this invention to provide improved compositions comprising novel lubricant compositions comprising the alkylated thianthrenes in accordance with the invention and novel lubricant and fuel compositions containing minor proportions of said thianthrenes as additives.

DESCRIPTION OF THE PREFERRED EMBODIMENTS

Broadly, the novel class of hydrocarbon products of the present invention can be characterized as adducts of a hydrocarbyl substituent precursor, which can contain one or more olefin groups, and a thianthrene. The hydrocarbyl substituted group can contain from $C_3-C_{500}$, preferably $C_6-C_{50}$ and most preferably $C_8-C_{18}$ The hydrocarbyl group can optionally contain S, N, O, P and/or F. The hydrocarbyl group can be alkyl, alkenyl, alkynyl, arylalkyl, aryl, aliphatic, cyclic, linear or branched. Substitution can be on one or more positions of the aromatic rings, with alkylation on either or both rings.

The preparation of these novel compositions may be by means of a thermal or catalytic addition reaction. The exact mechanism of the reaction is not important to the purposes of this invention, so long as the hydrocarbyl group becomes attached to the thianthrene described herein.

One preferred method of reaction between the hydrocarbyl substituent precursor and the thianthrene is the combination of these reactants in the presence of specific zeolite catalysts. Non-limiting examples are Octacat® USY, ZSM-12 and MCM-22. This reaction is affected at temperatures ranging from ambient to 350° C., preferably from 100–250° C. and most preferably from 180–240° C. over a period required to produce desired conversion of reactants to product. Optionally, the reaction can be performed in a batch or semi-batch mode by continuous or partial addition of the catalyst or hydrocarbyl group to the thianthrene. Catalyst can be used at levels ranging from 1 gram/mole of aromatic to 50 grams/mole of aromatic, and most preferably from 10–30 gram/mole of aromatic.

In general, the production of alkylated thianthrenes is favored by the use of zeolite catalysts such as zeolite beta or zeolite Y, preferably USY, of controlled acidity, preferably with an alpha value below about 200 and, for the best results, below 100, e.g., about 25–50.

The alpha value of the zeolite is an approximate indication of the catalytic cracking activity of the catalyst compared to a standard catalyst. The alpha test gives the relative rate constant (rate of normal hexane conversion per volume of catalyst per unit time) of the test catalyst relative to the standard catalyst which is taken as an alpha of 1 (Rate Constant=0.016 sec–1). The alpha test is described in U.S. Pat. No. 3,354,078 and In J. Catalysis, 4, 527 (1965); 6, 278 (1966); and 61, 395 (1980), to which reference is made for a description of the test. The experimental conditions of the test used to determine the alpha values referred to in this specification include a constant temperature of 538° C. and a variable flow rate as described in detail in J. Catalysis, 61, 395 (1980).

Optionally, the products of this invention can be prepared by reaction of the hydrocarbyl substituent precursor with thianthrene in the presence of $AlCl_3$ and other proton or Lewis acids as described in G. A. Olah's "Friedel-Crafts and Related Reactions", Vol. I, 1963, Interscience Publishers.

The alkylated thianthrenes produced by this process may be represented generally by the structure:

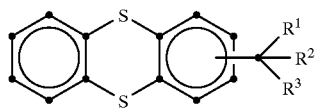

where $R_1$, $R_2$ or $R_3$ may be H, alkyl, alkenyl, alkynyl, aryl, alkylaryl, cyclic, linear or branched as previously described;

and/or where $R_1$, $R_2$ or $R_3$ can contain S, N, O, P and/or F;

and/or where $R_1$, $R_2$ or $R_3$ are linked to form a cyclic structure.

The hydrocarbon compositions of the present invention relate to improved thermally and oxidatively stable fluids. These may be used optionally as liquid lubricants or in liquid lubricant compositions, and as solid lubricants or in solid lubricant compositions including greases, such as polyurea, lithium carboxylate or clay-thickened greases.

These hydrocarbon compositions may also be used in combination with additives, for example, antioxidants, EP/antiwear agents, inhibitors, detergents and dispersants, and viscosity index improvers. Non-limiting examples of antioxidants include phenols which can be hindered and aromatic amines. Non-limiting examples of EP/antiwear additives include zinc phosphorodithioates, sulfurized esters, sulfurized olefins, phosphonates, phosphates, phosphorothionates, etc. Non-limiting examples of inhibitors include DMTD, phenothiazine, etc. Non-limiting examples of detergents and dispersants include sulfonates, phenates, and polymeric succinimides. These can be either metallic or non-metallic. Metallic detergents can be calcium or magnesium derived and can be neutral or over based.

The hydrocarbon compositions of this invention as noted hereinabove can be used alone or in combination with other synthetic and/or mineral oil fluids.

Fuel compositions are also contemplated for use herein, these include both hydrocarbon fuels, including gasoline, naphtha and diesel fuels or alcoholic fuels or mixtures of alcoholic and hydrocarbon fuels. Fuel compositions can contain 10 to 1000 pounds of alkylated thianthrene as additive per 1000 barrels of fuel or more preferably 25 to 250 pounds per 1000 barrels of fuel.

When the compositions of the present invention are used alone or in combination with other synthetic and/or mineral oil fluids, the below described oils of lubricating viscosity may be used.

In general, mineral oils, both paraffinic, naphthenic and mixtures thereof, employed as the lubricant, or grease vehicle, may be of any suitable lubricating viscosity range, as for example, from about 45 SSU at 100° F. to about 6000 SSU at 100° F. to about 6000 SSU at 100° F. and preferably, from about 50 to about 250 SSU at 210° F. These oils may have viscosity indexes ranging to about 95 are preferred. The average molecular weights of these oils may range from about 250 to about 800. Where the lubricant is to be employed in the form of a grease, the lubricating oil is generally employed in an amount sufficient to balance the total grease composition, after accounting for the desired quantity of the thickening agent, and other additive components to be included in the grease formulation.

A wide variety of materials may be employed as thickening or gelling agents. These may include any of the conventional metal salts or soaps, which are dispersed in the lubricating vehicle in grease-forming quantities in an amount to impart to the resulting grease composition the desired consistency. Other thickening agents that may be employed in the grease formulation may comprise the non-soap thickeners, such as surface-modified clays and silicas, aryl ureas, calcium complexes and similar materials. In general, grease thickeners may be employed which do not melt and dissolve when used at the required temperature within a particular environment; however, in all other respects, any materials which is normally employed for thickening or gelling hydrocarbon fluids for foaming grease can be used in preparing grease in accordance with the present invention.

In instances where synthetic oils, or synthetic oils employed as the lubricant or vehicle for the grease, are desired in preference to mineral oils, or in combination therewith, various compounds of this type may be successfully utilized. Typical synthetic oils include, but are not limited to, polyisobutylene, polybutenes, hydrogenated polydecenes, polypropylene glycol, polyethylene glycol, trimethylpropane esters, neopentyl and pentaerythritol esters, di(2-ethylhexyl) sebacate, di(2-ethylhexyl) adipate, dibutyl phthalate, fluorocarbons, silicate esters, silanes, esters of phosphorus-containing acids, liquid ureas, ferrocene derivatives, hydrogenated synthetic oils, chain-type polyphenyls, siloxanes and silicones (polysiloxanes), alkyl-substituted diphenyl ethers typified by a butyl-substituted bis(p-phenoxy phenyl) ether, phenoxy phenylethers.

When used above or as additives the materials in accordance with the invention also have improved antiwear and/or the ability to improve the antiwear characteristics and the additive solubility characteristics of various oleagenous materials to which may have been added such as the aforementioned hydrocarbyl lubricating media.

The following examples are exemplary only and are not intended to limit the invention.

EXAMPLE 1

To a vigorously stirred mixture of thianthrene (216.3 g, 1.0 mole) and 1-tetradecene (196 g, 1.0 mole) in a flask fitted with thermocouple and reflux condenser was added 15 g of FCC Octacat USY catalyst. The mixture was heated to 200° C. with stirring for six hours. After cooling to room temperature, the mixture was filtered to remove catalyst and vacuum distilled to 170° C. at 0.5–1.5 mmHg to remove unreacted starting materials and to obtain the desired thianthrene product.

EXAMPLE 2

Using the procedure in Example 1, thianthrene (216.3 g, 1.0 mole) and 1-tetradecene (196 g, 1.0 mole) were reacted using 30 grams of FCC Octacat USY catalyst.

EXAMPLE 3

Using the procedure in Example 1, thianthrene (216.3 g, 1.0 mole) and 1-dodecene (168.32 g, 1.0 mole) were reacted using 15 grams of FCC Octacat USY catalyst.

EXAMPLE 4

Using the procedure in Example 1, thianthrene (216.3 g, 1.0 mole) and 1-hexadecene (224 g, 1.0 mole) were reacted using 15 grams of FCC Octacat USY catalyst.

EXAMPLE 5

Using the procedure in Example 1, thianthrene (216.3 g, 1.0 mole) and 1-octadecene (252.5 g, 1.0 mole) were reacted using 15 grams of FCC Octacat USY catalyst.

EXAMPLE 6

To a stirred mixture of 1-octene (224.2 g, 2 moles), and thianthrene, 216.3 g (1 mole), was added 2.0 grams of anhydrous $AlCl_3$ and heated at reflux for six hours. The mixture was cooled, washed to remove inorganic materials, and dried over anhydrous $MgSO_4$ to obtain the desired hydrocarbyl thianthrene. Gas chromatographic analysis showed essentially complete reaction of starting material.

EXAMPLE 7

Using the procedure in Example 6, 1-decene, 140.27 g (1 mole) and thianthrene (216.3 g, 1 mole) were reacted with $AlCl_3$ (2 grams) at reflux for six hours. Vacuum distillation of the washed organic mixture to 170° C. at 0.5–1.5 mmHg resulted in the desired hydrocarbyl thianthrene product.

Typical properties of an exemplary hydrocarbyl thianthrene are shown in Table 1.

TABLE 1

| Hydrocarbyl | $C_{16}$ |
|---|---|
| KV @ 100° C., cSt | 12.9 |
| VI | 49 |
| Pour Point (° F.) | −4 |

PERFORMANCE EVALUATION AS A LUBRICANT IMPROVED ANTIWEAR

Hexadecene alkylated thianthrene was compared to polyolefin base stock in a Four-Ball Wear Test.

In the Four-Ball Wear Test, three stationary balls are placed in a lubricant cup and a lubricant containing the compound to be tested is added thereto, and a fourth ball is placed in a chuck mounted on a device which can be used to spin the ball at known speeds and loads. The examples were tested using half inch stainless steel balls of 52100 steel for thirty minutes under 30 kg load at 1800 rpm and 200° F. If additional information is desired consult test method ASTM D226 and/or U.S. Pat. No. 4,761,482.

In the Four-Ball EP Test the weld load, in KG force, is determined by the ASTM D-2596 Four-Ball EP test in which a steel ball, under a constant force or load, is rotated at a speed of 1770 RPM against three other balls held in a stationary position in the form of a cradle. The temperature is maintained at 100° C. and the rotating ball is subjected to successively higher loads for 10 seconds until the four balls weld together. The results are summarized in Table 3 below.

K (as reported in Table 2) the wear coefficient is calculated from the wear volume, V, of the stationary ball. The wear volume is calculated from the wear scar diameter D in mm as follows:

V=[15.5 D3−0.001033L] D×103 mm3 where L is the machine load in kg. This equation considers the elastic deformation of the steel balls.

Wear Coefficient K
Dimensionless K is defined as $$K = \frac{VH}{dN}$$

where V=wear volume, mm3
H=hardness 9725 kg/mm2 for 52100 steel
d=(23.3 mm/rev) (RPH×Time)
N=(0.408) (Load in kg)
f=the Coefficient of Friction
LNS=Last Non Seizure Load
LWI=Load Wear Index

TABLE 2

Four-Ball Wear Test Results (200° F./40 Kg/30 min)

| | 1800 RPM | |
|---|---|---|
| | K factor | f |
| $C_{16}$-thianthrene | 11.7 | 0.091 |
| Commercial Synthetic Lubricant | 402 | 0.076 |

TABLE 3

Four-Ball EP (100° C.)

| | LNS | LWI | Weld |
|---|---|---|---|
| $C_{16}$-thianthrene | 32 | 24.6 | 160 |
| Commercial Synthetic Lubricant | 32 | 14.6 | 160 |

The results show that the alkylated thianthrene produced less wear than the other base stock, with an improvement of coefficient of friction (f). The alkylated thianthrene also had significantly improved LWI and Weld values.

The Four-Ball Test results clearly demonstrate the excellent antiwear properties of these compositions.

PERFORMANCE AS A LUBRICANT IMPROVED ANTI-WEAR

To a synthetic lubricant base stock was added 4.0 wt % of sulfurized isobutylene (as generally described by A. G. Horodysky in U.S. Pat. No. 3,703,504) and 0.5 wt % of a hindered phenolic inhibitor obtained from Ethyl Corp. as Ethyl 702. The mixture of additives was insoluble in the base stock and the sample was cloudy. To this mixture was added 21 wt % $C_{14}$ alkylated thianthrene. The sample was mixed; the additives completely dissolved and the mixture became clear.

Light stability was good as no color change or precipitate was observed over one month.

The use of alkylated thianthrene as a suitable replacement for components of current lubricant formulations is highly desirable. For example, synthetic and/or mineral based lubricant composition containing esters for improved additive solubility would be significantly improved by replacement with alkylated thianthrene due to its excellent thermal stability and excellent additive solubility. Alkyl thianthrenes prepared as described herein provide excellent base stock properties and could themselves serve as the base stock in formulations for various application, for example, applications where high temperatures are maintained.

Although the present invention has been described with preferred embodiments, it is to be understood that modifications and variations may be resorted to, without departing from the spirit and scope of this invention, as those skilled in the art will readily understand. Such variations and modifications are considered within the purview and scope of the appended claims.

What is claimed is:

1. A process for the preparation of a high-temperature stable monoalkylated lubricant fluid or lubricant additive comprising catalytically reacting in the presence of a zeolite catalyst selected from the group consisting of zeolite beta, zeolite Y, ZSM-12 and MCM-22 (1) a hydrocarbyl substituent precursor, having at least one olefinic group and optionally containing S, N, O, P, F, or mixtures thereof, and (2) a thianthrene and wherein said hydrocarbyl substituent is selected from the group consisting of alkyl, alkenyl, alkynyl, arylalkyl, or aryl, cyclic or linear containing from 3 to about 500 carbons wherein the reaction temperature varies from ambient to.about 350° C., the molar ratio of said hydrocarbyl substituent precursor substituent to thianthrene varies from 1:1 to about 10:1 and the amount of catalyst varies from 5 to about 100 grams of catalyst to about 1 mole of thianthrene.

2. The process of claim 1 wherein the catalyst is FCC USY or MCM-22.

3. The process of claim 2 wherein the catalyst is FCC USY.

4. The process of claim 3 wherein the reactants are 1-tetradecene and thianthrene and the catalyst is FCC USY.

5. The process of claim 3 wherein the reactants are 1-dodecene and thianthrene and the catalyst is FCC USY.

6. The process of claim 3 wherein the reactants are 1-hexadecene and thianthrene and the catalyst is FCC USY.

7. The process of claim 3 wherein the reactants are 1-octadecene and thianthrene and the catalyst is FCC USY.

8. A high temperature stable lubricant fluid comprising a monoalkylated adduct prepared by catalytically reacting in the presence of a zeolite catalyst selected from the group consisting of zeolite beta, zeolite Y, ZSM-12 and MCM-22 (1) a hydrocarbyl substituent precursor, having at least one olefinic group and optionally containing S, N, O, P, F, or mixtures thereof, and (2) a thianthrene and wherein said hydrocarbyl substituent is selected from the group consisting of alkyl, alkenyl, alkynyl, arylalkyl, or aryl, cyclic or linear containing from 3 to about 500 carbons wherein the reaction temperature varies from ambient to about 350° C., the molar ratio of said hydrocarbyl substituent precursor to thianthrene varies from 1:1 to about 10:1 and the amount of catalyst varies from 5 to about 100 grams of catalyst to about 1 mole of thianthrene wherein said hydrocarbyl thianthrene adduct comprises a major proportion of said lubricant fluid and an oil of lubricating viscosity comprises a minor proportion of said lubricant fluid.

* * * * *